United States Patent
Roh

(10) Patent No.: US 9,414,958 B1
(45) Date of Patent: Aug. 16, 2016

(54) SEXUAL AID SYSTEMS

(76) Inventor: Steven M. Roh, Tempe, AZ (US)

(*) Notice: Subject to any disclaimer, the term of this patent is extended or adjusted under 35 U.S.C. 154(b) by 1007 days.

(21) Appl. No.: 12/841,085

(22) Filed: Jul. 21, 2010

Related U.S. Application Data

(60) Provisional application No. 61/229,706, filed on Jul. 29, 2009.

(51) Int. Cl.
*A61F 5/41* (2006.01)

(52) U.S. Cl.
CPC ........................................ *A61F 5/41* (2013.01)

(58) Field of Classification Search
CPC ...... A61F 5/41; A61F 2005/414; A61J 19/30; A61J 19/32; A61J 19/34
USPC .............. 600/38–41; 601/57, 67, 71, 79, 132, 601/143, 144
See application file for complete search history.

(56) References Cited

U.S. PATENT DOCUMENTS

| | | | |
|---|---|---|---|
| 1,608,806 A * | 11/1926 | Nelson | 600/41 |
| 3,461,863 A | 8/1969 | Sullinger | |
| 3,773,040 A | 11/1973 | Gavrilovich | |
| 5,027,800 A | 7/1991 | Rowland | |
| 5,085,209 A | 2/1992 | Gottschalk | |
| 5,221,251 A | 6/1993 | Edminster | |
| 5,690,603 A | 11/1997 | Kain | |
| 5,855,548 A * | 1/1999 | Place | 600/38 |
| 5,954,631 A | 9/1999 | Gorsuch | |
| 2005/0155609 A1 | 7/2005 | Lin | |
| 2007/0038019 A1* | 2/2007 | Weng | 600/38 |

* cited by examiner

*Primary Examiner* — Samuel Gilbert

(57) ABSTRACT

A sexual aid system including a flexible fabric tube and tube-insertable vibrator to assist a user to maintain an erection and offer additional stimulation to one or both partners in combination with user-adjustability for fit and vibrator location.

20 Claims, 5 Drawing Sheets

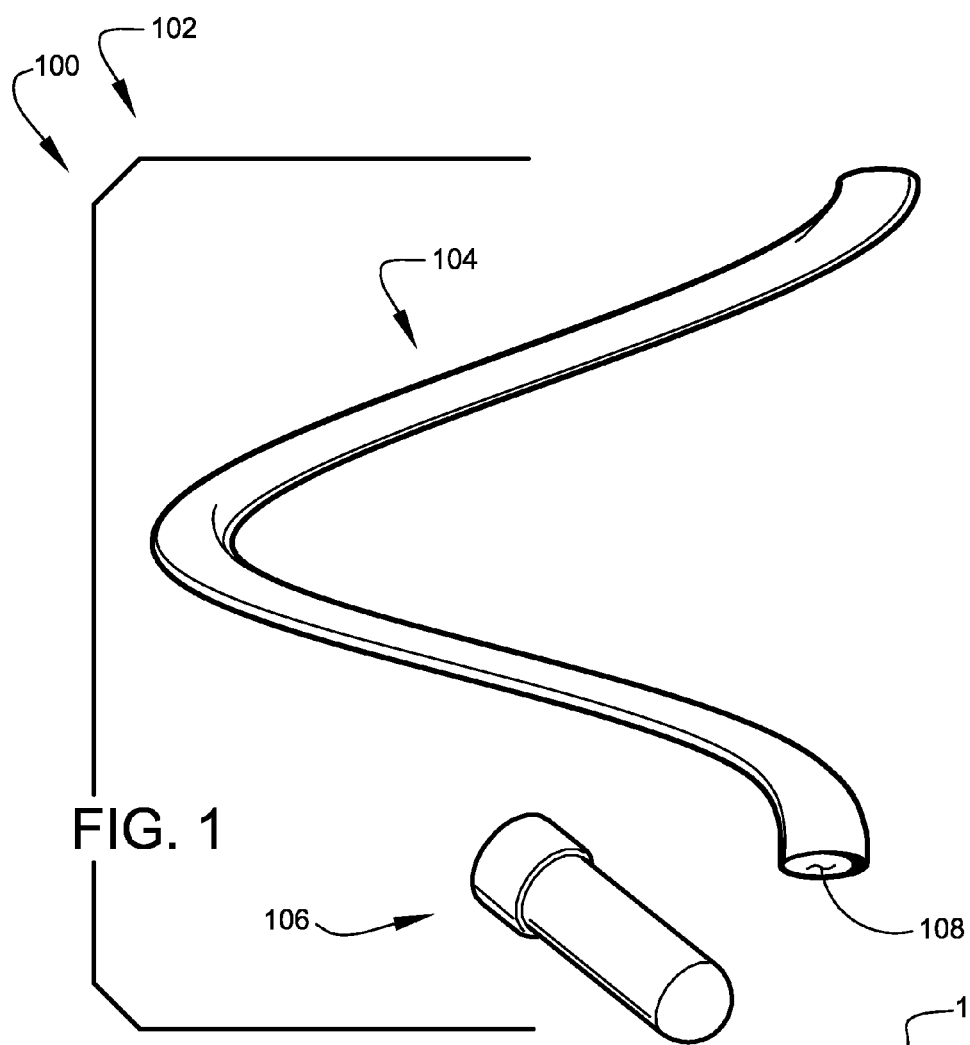
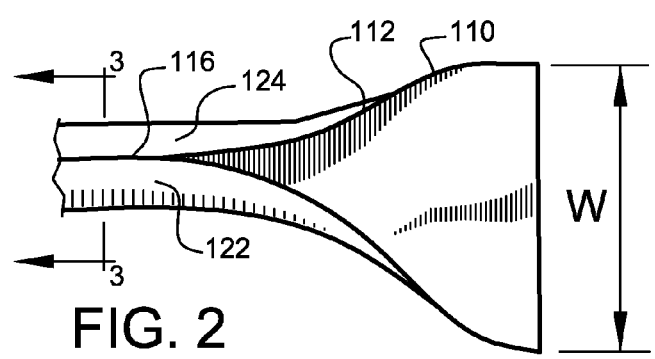
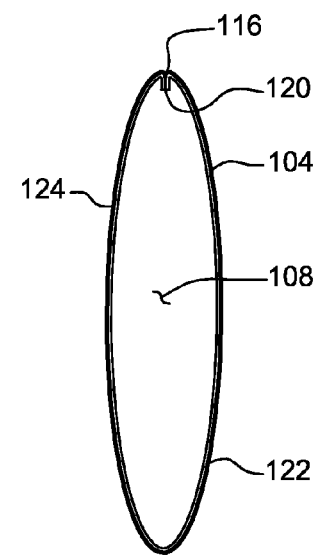

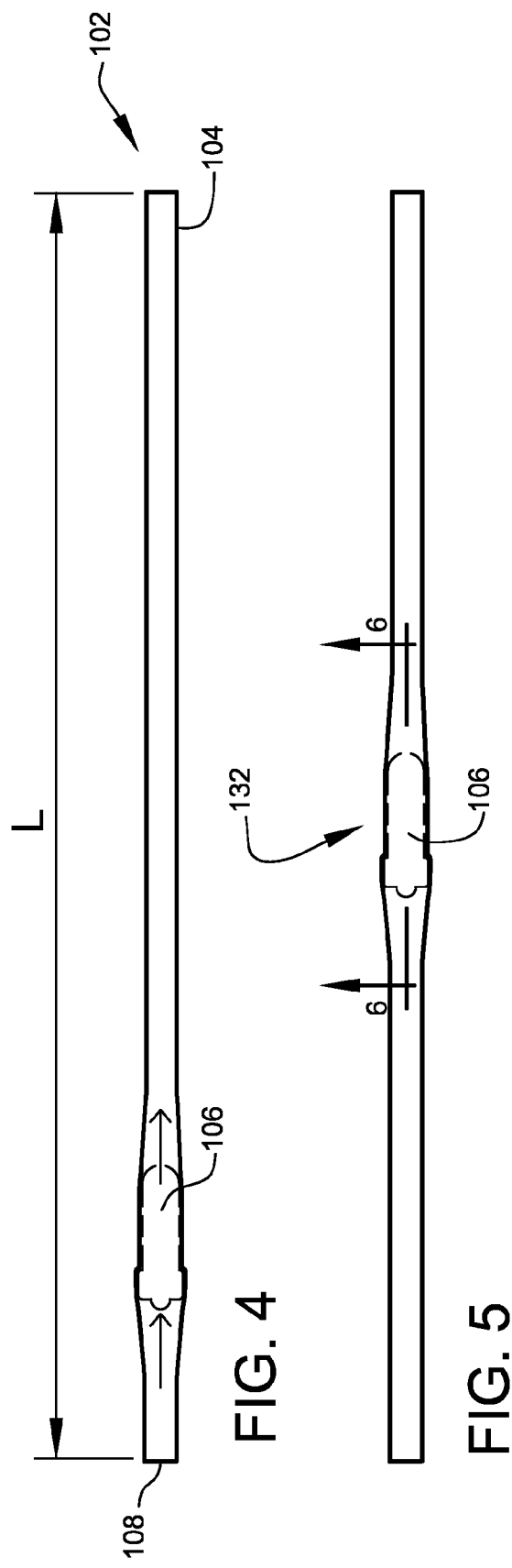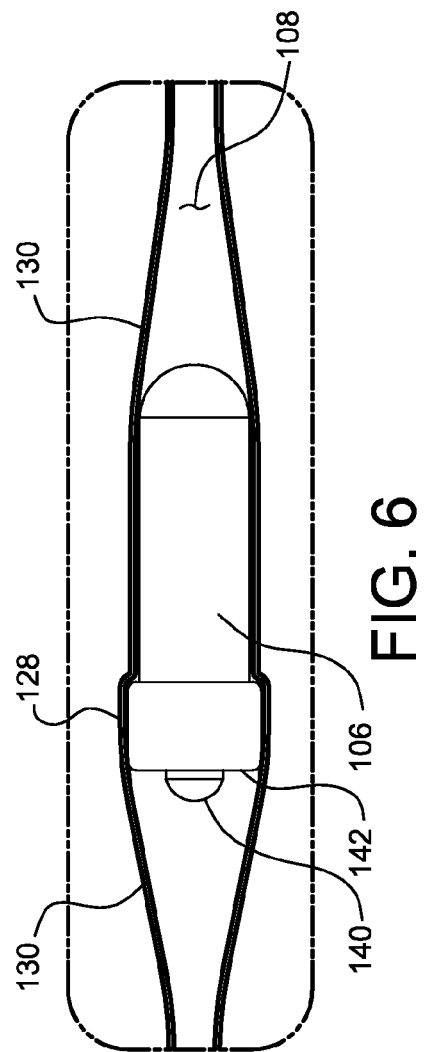

SEXUAL AID SYSTEMS

CROSS-REFERENCE TO RELATED APPLICATION

The present application is related to and claims priority from prior provisional application Ser. No. 61/229,706, filed Jul. 29, 2009, entitled "SEXUAL AID SYSTEMS", the contents of which is incorporated herein by this reference and is not admitted to be prior art with respect to the present invention by the mention in this cross-reference section.

BACKGROUND

This invention relates to providing a sexual aid system to improve control of human penile erection combined with sexual stimulation. More particularly, this invention relates to providing a sexual aid system relating to combining comfort, user-controlled cinching, and vibrator elements with improved control and maintaining of a human penile erection.

Many sexual aids are available today to aid both men and women in sexual function and stimulation. Men, in particular, may suffer from issues relating to maintaining an erection during coitus. Devices to assist maintaining erection of the penis are most often restrictive and offer little adjustability as to size and fit. Further, combinations of sexual aids to maintain erection and offer additional stimulation to one or both partners in combination with user-adjustability for fit and stimulation location are limited.

OBJECTS AND FEATURES OF THE INVENTION

A primary object and feature of the present invention is to provide a system overcoming the above-mentioned problem(s).

It is a further object and feature of the present invention to provide such a system that offers a sexual aid that assists maintaining penile erection in combination with vibration stimulation to one or both partners in combination with user-adjustability for fit and stimulation location.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a sexual aid kit, relating to assisting at least one user to maintain a voluntary penis erection, comprising: at least one vibrator structured and arranged to provide vibratory movement; and at least one flexible tube, having a single longitudinal internal chamber, structured and arranged to hold such at least one vibrator; wherein such at least one flexible tube comprises at least one restrictor structured and arranged to restrict longitudinal movement of such at least one vibrator when such at least one vibrator is within such at least one restrictor; and wherein such at least one flexible tube comprises at least one cinchable segment structured and arranged to cinch such at least one flexible tube about a human penis. Moreover, it provides such a sexual aid kit further comprising at least one storage pouch structured and arranged to store the sexual aid kit. Additionally, it provides such a sexual aid kit further comprising: at least one package structured and arranged to hold the contents of such at least one accessory sexual aid kit; and at least one set of instructions.

In accordance with another preferred embodiment hereof, this invention provides a sexual aid system, relating to assisting at least one user to maintain a voluntary penis erection, comprising: at least one vibrator structured and arranged to provide vibratory movement; and at least one flexible tube, having a single longitudinal internal chamber, structured and arranged to hold such at least one vibrator; wherein such at least one flexible tube comprises at least one restrictor structured and arranged to restrict longitudinal movement of such at least one vibrator when such at least one vibrator is within such at least one restrictor; and wherein such at least one flexible tube comprises at least one cinchable segment structured and arranged to cinch such at least one flexible tube about a human penis. Also, it provides such a sexual aid system wherein such at least one flexible tube comprises fabric.

In addition, it provides such a sexual aid system wherein such at least one flexible tube comprises entirely fabric structured and arranged to be seamed by radio frequency weld. And, it provides such a sexual aid system wherein such fabric is seamed by radio frequency weld. Further, it provides such a sexual aid system wherein such at least one flexible tube is about 12 to about 14 inches in length. Even further, it provides such a sexual aid system wherein such at least one flexible tube comprises a maximum internal diameter of about ½ inch to about ¾ inch. Moreover, it provides such a sexual aid system wherein such at least one vibrator comprises a maximum external diameter of about ½ inch to about ¾ inch. In accordance with another preferred embodiment hereof, this invention provides a sexual aid system, relating to assisting at least one user to maintain a voluntary penis erection, comprising: at least one vibrator structured and arranged to provide vibratory movement; and at least one flexible tube, having a single longitudinal internal chamber, structured and arranged to hold such at least one vibrator; wherein such at least one flexible tube comprises at least one restrictor structured and arranged to restrict longitudinal movement of such at least one vibrator when such at least one vibrator is within such at least one restrictor; wherein such at least one flexible tube comprises at least one cinchable segment structured and arranged to cinch such at least one flexible tube about a human penis; wherein such at least one flexible tube comprises woven fabric; wherein such at least one flexible tube is about 12 to about 14 inches in length; and wherein such at least one flexible tube comprises a maximum internal diameter of about ½ inch to about ¾ inch.

Additionally, it provides such a sexual aid system wherein such woven fabric comprises polyester. Also, it provides such a sexual aid system wherein such at least one flexible tube comprises entirely woven fabric. In addition, it provides such a sexual aid system wherein such woven fabric is seamed by radio frequency weld. And, it provides such a sexual aid system wherein such at least one vibrator comprises a maximum external diameter of about ½ inch to about ¾ inch.

In accordance with another preferred embodiment hereof, this invention provides such a sexual aid system comprising a sexual aid method comprising the steps of: providing at least one stretchable soft-fabric tube; providing at least one vibrator having at least one larger diameter than such at least one stretchable soft-fabric tube; placing such at least one vibrator within such at least one stretchable soft-fabric tube; tying such at least one stretchable soft-fabric tube around at least one human penis to form at least one knot; and cinching such at least one knot to a user-desired restriction; wherein such user is enabled to enhance sexual pleasure.

Further, it provides such a sexual aid system comprising a sexual aid method wherein such at least one stretchable soft-fabric tube comprises essentially one-hundred-percent polyester fabric. Even further, it provides such a sexual aid method wherein such one-hundred-percent polyester fabric is seamed by radio frequency weld.

In accordance with another preferred embodiment hereof, this invention provides a sexual aid system, relating to assisting at least one user to maintain a voluntary penis erection, comprising: vibrator means for providing vibratory movement; and flexible tube means for holding such vibrator means wherein such flexible tube means comprises restrictor means for restricting longitudinal movement of such vibrator means when such vibrator means is within such hollow means; and wherein such flexible tube means comprises cinchable segment means for cinching such flexible tube means about a human penis.

In accordance with another preferred embodiment hereof this invention provides such a sexual aid system comprising each and every novel feature, element, combination, step and/or method disclosed or suggested by this patent application.

BRIEF DESCRIPTION OF THE DRAWINGS

FIG. 1 shows a perspective view, illustrating a sexual aid of the sexual aid system, according to a preferred embodiment of the present invention.

FIG. 2 shows a perspective view, illustrating preferred seam arrangements and dimensions of a flexible tube of the sexual aid, according to a preferred embodiment of FIG. 1.

FIG. 3 shows the sectional view 3-3 of FIG. 2.

FIG. 4 shows a side elevation view, partially in section, illustrating preferred dimensions of the sexual aid according to the preferred embodiment of FIG. 1.

FIG. 5 shows a side elevation view, partially in section, of the sexual aid according to the preferred embodiment of FIG. 1.

FIG. 6 shows the sectional view 6-6 of FIG. 5.

Figure 8:
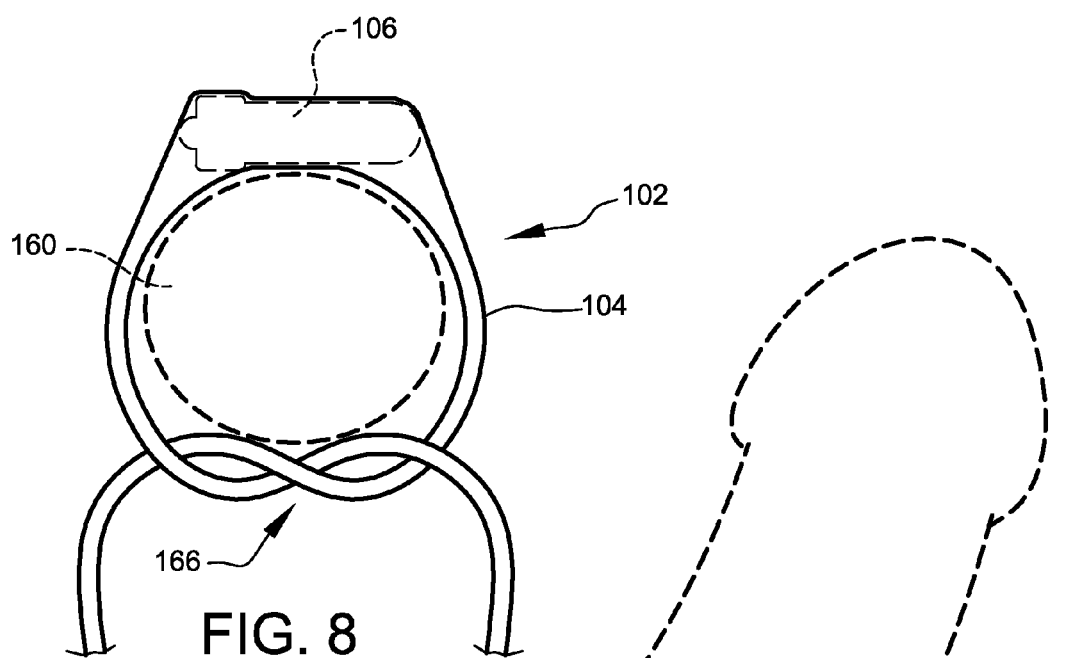
FIG. 8 shows a side view, partially in section, further illustrating a preferred use of the sexual aid, according to the preferred embodiment of FIG. 7.

DETAILED DESCRIPTION OF THE BEST MODES AND PREFERRED EMBODIMENTS OF THE INVENTION

FIG. 1 shows a perspective view, illustrating a sexual aid 102 of the sexual aid system 100, according to a preferred embodiment of the present invention. Sexual aid 102 preferably comprises a single flexible tube 104, preferably having a longitudinal hollow throughout, and a vibrator 106, preferably insertable within the hollow 108 of the single flexible tube 104, as shown. This arrangement at least embodies herein flexible tube means for holding said vibrator means; and, at least embodies herein at least one flexible tube, having a single longitudinal internal chamber, structured and arranged to hold said at least one vibrator.

FIG. 2 shows a perspective view, illustrating preferred seam arrangements and dimensions of a flexible tube of the sexual aid, according to a preferred embodiment of FIG. 1. FIG. 3 shows the sectional view 3-3 of FIG. 2. FIG. 4 shows a side elevation view, partially in section, illustrating preferred dimensions of the sexual aid 102 according to the preferred embodiment of FIG. 1.

Flexible tube 104 preferably is essentially comprised of fabric, preferably woven fabric, preferably having elastic characteristic to allow at least resilient expansion of the flexible tube 104 in diameter; and, preferably comprising "ultra-low friction" qualities to reduce friction against the skin and/or genitals when in use, as well as preferably comprising a higher co-efficient of friction against itself (fabric to fabric) to assist cinching (at least embodying herein wherein said flexible tube means comprises cinchable segment means for cinching said flexible tube means about a human penis; and, at least embodies herein wherein said at least one flexible tube comprises at least one cinchable segment structured and arranged to cinch said at least one flexible tube about a human penis). Woven fabric preferably is Rainwood "butter suede" woven fabric—soft-brushed one-hundred percent polyester finish—available in multiple colors from Hancock Fabrics Inc (available through http://www.hancockfabrics.com).

Flexible tube 104 is preferably made from a single strip of fabric 110 measuring about 12 to about 14 inches in length "L" and about 2¼ inches in width "W", as shown. To form flexible tube 104 single strip of fabric 110 preferably is folded in half lengthwise and seamed together along its open longitudinal edge 112 (leaving both traverse ends open). Preferably, seam 116 of flexible tube 104 is constructed utilizing a radio frequency weld (RF weld) preferably as done by Celina Industries 5373 State Route 29 Celina, Ohio 45822 USA (http://www.cutsealsew.com/contract-fabric-welding.htm).

In another preferred embodiment, if stitched utilizing thread, seam 116 is sewn together. In both the above preferred embodiments, flexible tube 104 is turned inside out after seaming so the stitching 120 is on the inside of the tube (See FIG. 3) leaving a smooth surface 124 on the exterior 122 of the flexible tube 104, as shown.

FIG. 5 shows a side elevation view, partially in section, of the sexual aid 102 according to the preferred embodiment of FIG. 1. FIG. 6 shows the sectional view 6-6 of FIG. 5. Vibrator 106 preferably is sized to fit into hollow 108, preferably comprising a push button controller 140, alternately preferably a dial controller, preferably located on end 142 of vibrator 106, preferably having more than one speed, preferably at least 3 speeds, as shown. Preferably, vibrator 106 is powered by battery, preferably watch batteries (LR44 or CR2, for example). Vibrator 106 (at least embodying herein vibrator means for providing vibratory movement; and, at least embodying herein at least one vibrator structured and arranged to provide vibratory movement) is preferably a TOPCO micro-mini vibrator having about a ½ inch to about a ¾ inch diameter, preferably about ⅝ inch diameter (sold by ADAM & EVE signature toys at least available at http://www.topcosales.us/).

Vibrator 106 is preferably supplied with flexible tube 104; however, upon reading this specification, those with ordinary skill in the art will now appreciate that, under appropriate circumstances, considering such issues as design preference, user preferences, marketing preferences, cost, structural requirements, available materials, technological advances, etc., other vibrators such as those available in the marketplace, etc., may suffice.

Vibrator 106 is preferably user-placed into the hollow 108 of flexible tube 104, preferably pushed by hand along the exterior 122 of flexible tube 104 until vibrator 106 is about in the center 132 of the flexible tube 104, as shown. Alternately preferably, vibrator 104 may be user-positioned almost anywhere in flexible tube 104 as desired by such user. Upon reading this specification, those with ordinary skill in the art will now appreciate that, under appropriate circumstances, considering such issues as, user anatomy, user preferences, etc., other vibrator placements such as, for example, along the bottom or sides of the penis, etc., may suffice.

Preferably, as stated above, fabric 110 provides resilient expansion of flexible tube 104 in diameter which provides qualities of an expander 128 to allow entry of vibrator 106 into the flexible tube 104 and a restrictor 130 (at least embodying herein wherein said flexible tube means comprises restrictor means 130 for restricting longitudinal movement of said vibrator means when said vibrator means is within said hollow means; and, at least embodying herein wherein said at least-one flexible tube comprises at least one restrictor structured and arranged to restrict longitudinal movement of said at least one vibrator when said at least one vibrator is within said at least one restrictor) to assist keeping vibrator 106 in place in the hollow 108 when and where vibrator 106 is placed into hollow 108 of flexible tube 104, as shown. In such manner, the fabric 110 qualities of flexible tube 104 as described above provide multiple functions to assist and create the sexual aid 102 of the present invention.

Further, upon reading this specification, those with ordinary skill in the art will now appreciate that, under appropriate circumstances, considering such issues as design preference, user preferences, marketing preferences, cost, structural requirements, available materials, technological advances, etc., other sexual devices placed into flexible tube 104 such as, for example, hot or cold liquid containers, metal balls, other vibration devices, etc., may suffice.

Figure 7:
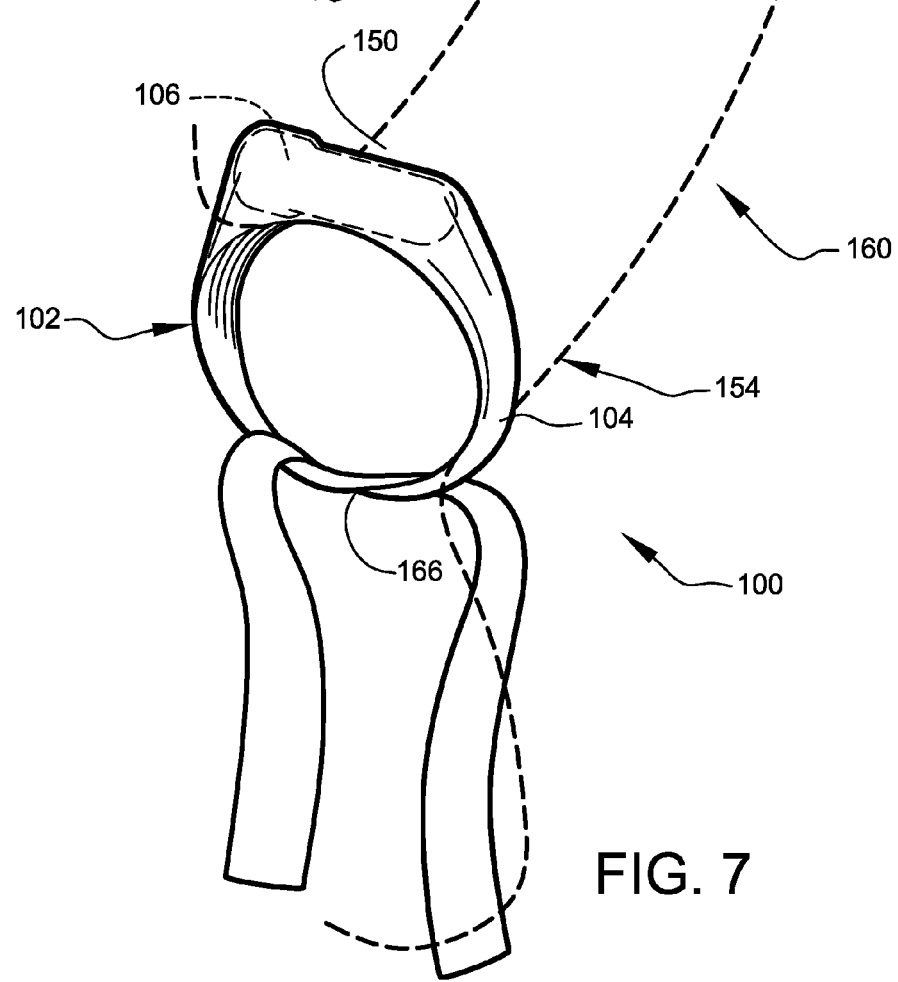
FIG. 7 shows a perspective view, illustrating a preferred use of the sexual aid of the sexual aid system, according to a preferred embodiment of the present invention.

FIG. 7 shows a perspective view, illustrating a preferred use of the sexual aid 102 of the sexual aid system 100, according to a preferred embodiment of the present invention. FIG. 8 shows a side view, partially in section, further illustrating a preferred use of the sexual aid 102, according to the preferred embodiment of FIG. 7. In use, sexual aid 102 preferably is used as follows: inserting vibrator 106 into flexible tube 104; arranging vibrator 106 in such position to increase sexual stimulation, preferably along the top 150 of the base 154 of the penis 160 (preferably to assist sexual pleasure for a female partner); tying flexible tube 104 around the base 154 of a human penis 160, preferably adjacent the pubic bone; forming at least one knot in such flexible tube 104, preferably a simple overhand knot 166, as shown; and, cinching such at least one knot to a user-desired restriction wherein such user is enabled to enhance sexual pleasure (preferably tight enough to restrict blood flow out of the penis and maintain turgidity of the penis). Upon reading this specification, those with ordinary skill in the art will now appreciate that, under appropriate circumstances, considering such issues as, user anatomy, user preferences, etc., other cinching placements such as, for example, along the top or sides of the penis, etc., may suffice.

Figure 9:
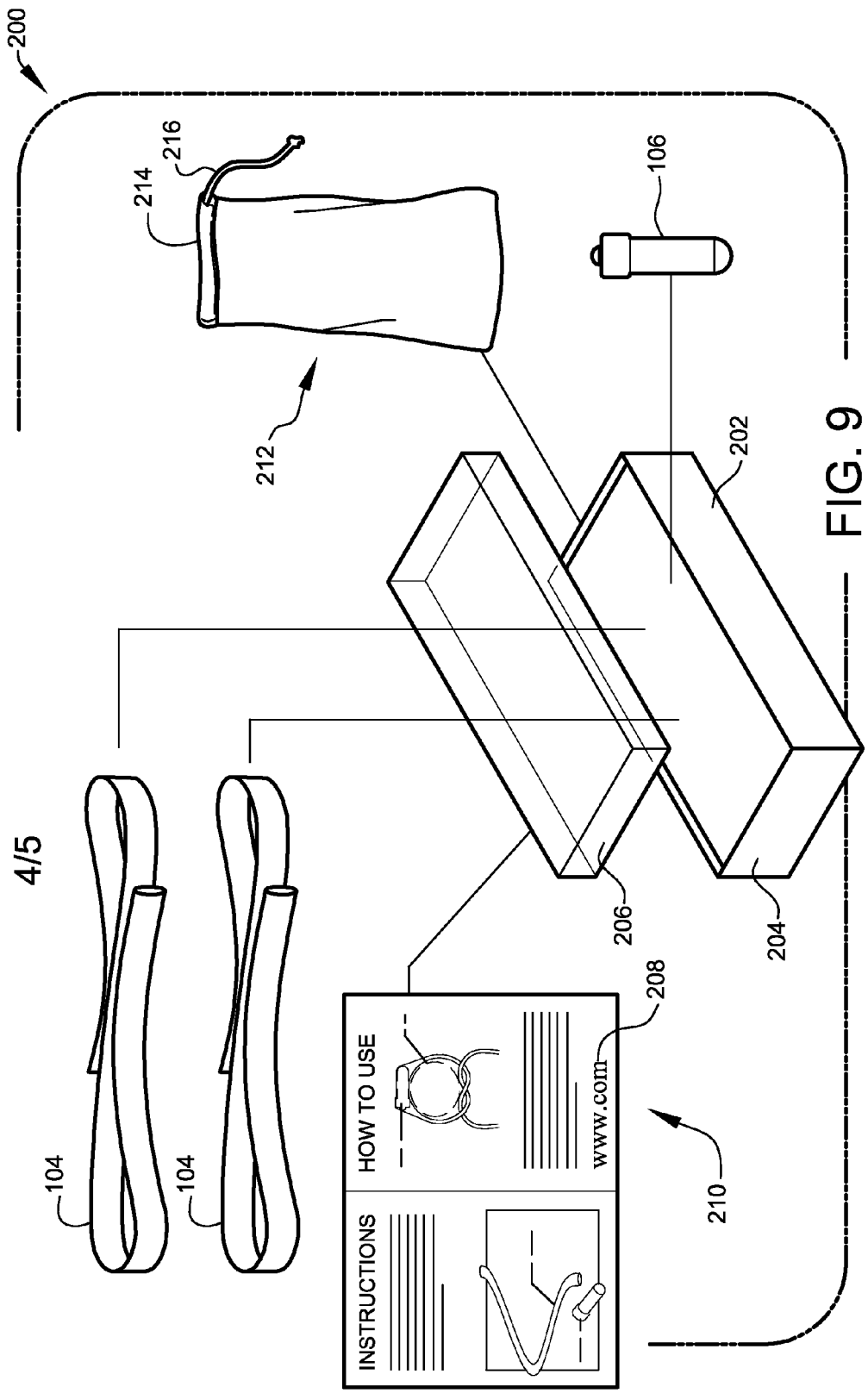
FIG. 9 shows a perspective view, illustrating a sexual aid kit of the sexual aid system, according to a preferred embodiment of the present invention.

FIG. 9 shows a perspective view, illustrating a sexual aid kit 200 of the sexual aid system 100, according to a preferred embodiment of the present invention. Sexual aid kit 200 preferably comprises at least one package 202 to house the contents of the sexual aid kit 200, preferably comprising a box 204 having at least one lid 206, as shown. Preferably, sexual aid kit 200 comprises at least one vibrator 106, at least one flexible tube 104, preferably two flexible tubes 104 (comprising preferred materials as described herein), and a set of instructions 210 comprising at least use and care instructions for sexual aid 102. Alternately preferably, a website address 208 to provide a web address for ordering additional product is also printed on instructions 210, as shown. Alternately preferably, sexual aid kit 200 comprises at least one pouch 212, preferably a soft satin fabric pouch, preferably having at least one closure 214, preferably a drawstring 216, as shown. Upon reading this specification, those with ordinary skill in the art will now appreciate that, under appropriate circumstances, considering such issues as design preference, user preferences, marketing preferences, cost, shipping requirements, available materials, technological advances, etc., other kit arrangements such as, for example, additional components, different packaging, multiple vibrators, etc., may suffice.

Preferably, all the components are placed into package 202 and offered for sale through brick and mortar locations or through Internet websites.

Figure 10:
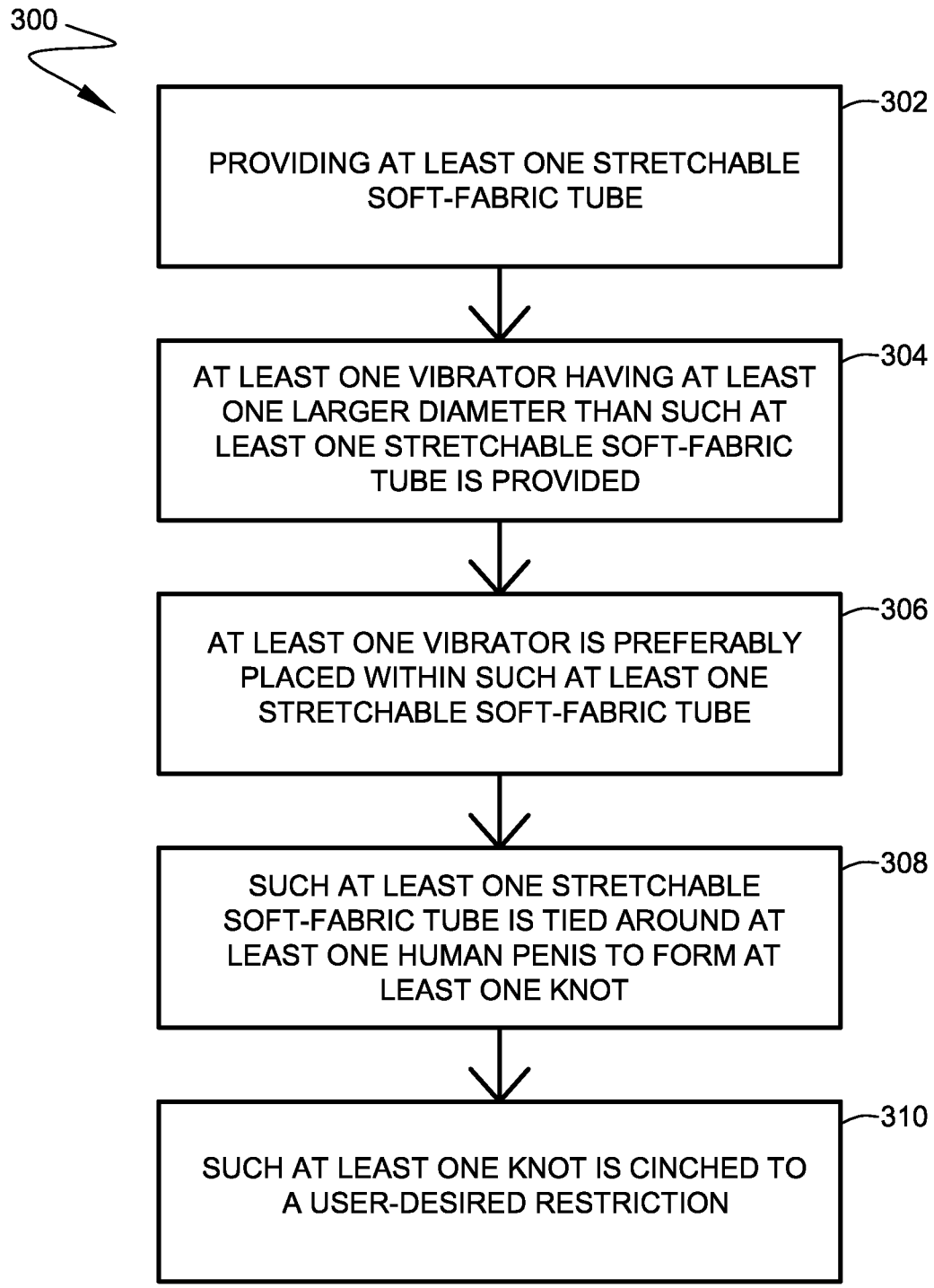
FIG. 10 shows a schematic diagram illustrating a preferred method of the present invention.

FIG. 10 shows a schematic diagram illustrating a preferred method 300 of the present invention. Method 300 preferably comprises a set of preferred steps, preferably beginning with providing at least one stretchable soft-fabric tube, as provided in preferred step 302. Next, at least one vibrator having at least one larger diameter than such at least one stretchable soft-fabric tube is provided, as provided in preferred step 304. Next, at least one vibrator is preferably placed within such at least one stretchable soft-fabric tube, as provided in preferred step 306. Next, such at least one stretchable soft-fabric tube is tied around at least one human penis to form at least one knot, as provided in preferred step 308. Next, such at least one knot is cinched to a user-desired restriction, as provided in preferred step 310, wherein such user is enabled to enhance sexual pleasure.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A sexual aid kit, relating to assisting at least one user to maintain a voluntary penis erection, comprising:
    a) at least one vibrator structured and arranged to provide vibratory movement; and
    b) at least one flexible tube, having a single longitudinal internal chamber, structured and arranged to hold said at least one vibrator;
    c) wherein said at least one flexible tube comprises at least one restrictor structured and arranged to restrict longitudinal movement of said at least one vibrator when said at least one vibrator is within said at least one restrictor; and
    d) wherein said at least one flexible tube comprises at least one cinchable segment structured and arranged to cinch said at least one flexible tube about a human penis.

2. The sexual aid kit according to claim 1 further comprising at least one storage pouch structured and arranged to store the sexual aid kit.

3. The sexual aid kit according to claim 1 further comprising:
    a) at least one package structured and arranged to hold the at least one vibrator and the at least one flexible tube of said sexual aid kit; and
    b) at least one set of instructions.

4. A sexual aid system, relating to assisting at least one user to maintain a voluntary penis erection, comprising:
   a) at least one vibrator structured and arranged to provide vibratory movement; and
   b) at least one flexible tube, having a single longitudinal internal chamber, structured and arranged to hold said at least one vibrator;
   c) wherein said at least one flexible tube comprises at least one restrictor structured and arranged to restrict longitudinal movement of said at least one vibrator when said at least one vibrator is within said at least one restrictor; and
   d) wherein said at least one flexible tube comprises at least one cinchable segment structured and arranged to cinch said at least one flexible tube about a human penis.

5. The sexual aid system according to claim 4 wherein said at least one flexible tube comprises fabric.

6. The sexual aid system according to claim 4 wherein said at least one flexible tube comprises entirely fabric structured and arranged to be seamed by radio frequency weld.

7. The sexual aid system according to claim 6 wherein said fabric is seamed by radio frequency weld.

8. The sexual aid system according to claim 4 wherein said at least one flexible tube is about 12 to about 14 inches in length.

9. The sexual aid system according to claim 4 wherein said at least one flexible tube comprises a maximum internal diameter of about ½ inch to about ¾ inch.

10. The sexual aid system according to claim 4 wherein said at least one vibrator comprises a maximum external diameter of about ½ inch to about ¾ inch.

11. A sexual aid system, relating to assisting at least one user to maintain a voluntary penis erection, comprising:
   a) at least one vibrator structured and arranged to provide vibratory movement; and
   b) at least one flexible tube, having a single longitudinal internal chamber, structured and arranged to hold said at least one vibrator;
   c) wherein said at least one flexible tube comprises at least one restrictor structured and arranged to restrict longitudinal movement of said at least one vibrator when said at least one vibrator is within said at least one restrictor;
   d) wherein said at least one flexible tube comprises at least one cinchable segment structured and arranged to cinch said at least one flexible tube about a human penis;
   e) wherein said at least one flexible tube comprises woven fabric;
   f) wherein said at least one flexible tube is about 12 to about 14 inches in length; and
   g) wherein said at least one flexible tube comprises a maximum internal diameter of about ½ inch to about ¾ inch.

12. The sexual aid system according to claim 11 wherein said woven fabric comprises polyester.

13. The sexual aid system according to claim 12 wherein said at least one flexible tube comprises entirely woven fabric.

14. The sexual aid system according to claim 13 wherein said woven fabric is seamed by radio frequency weld.

15. The sexual aid system according to claim 12:
   a) wherein said polyester fabric comprises a higher co-efficient of friction fabric-to-fabric as compared to fabric-to-penis; and
   b) wherein cinchability of said at least one flexible tube about a human penis is assisted.

16. The sexual aid system according to claim 11 wherein said at least one vibrator comprises a maximum external diameter of about ½ inch to about ¾ inch.

17. A sexual aid method comprising the steps of:
   a) providing at least one stretchable soft-fabric tube;
   b) providing at least one vibrator having at least one larger diameter than said at least one stretchable soft-fabric tube;
   c) placing said at least one vibrator within such said at least one stretchable soft-fabric tube;
   d) tying said at least one stretchable soft-fabric tube around at least one human penis to form at least one knot; and
   e) cinching said at least one knot to a user-desired restriction;
   f) wherein a user is enabled to enhance sexual pleasure.

18. The sexual aid method according to claim 17 wherein said at least one stretchable soft-fabric tube comprises one-hundred-percent polyester fabric.

19. The sexual aid method according to claim 18 wherein said one-hundred-percent polyester fabric is seamed by radio frequency weld.

20. A sexual aid system, relating to assisting at least one user to maintain a voluntary penis erection, comprising:
   a) vibrator means for providing vibratory movement; and
   b) flexible tube means for holding said vibrator means
   c) wherein said flexible tube means comprises restrictor means for restricting longitudinal movement of said vibrator means when said vibrator means is within said flexible tube means; and
   d) wherein said flexible tube means comprises cinchable segment means for cinching said flexible tube means about a human penis.

* * * * *